United States Patent [19]
Guthikonda et al.

[11] Patent Number: 5,908,842
[45] Date of Patent: Jun. 1, 1999

[54] SUBSTITUTED 2-ACYLAMINO-PYRIDINES AS INHIBITORS OF NITRIC OXIDE SYNTHASE

[75] Inventors: Ravindra Guthikonda; William Hagmann; Malcolm Maccoss; Shrenik Shah; Philippe Durette, all of Rahway, N.J.

[73] Assignee: Merck & Co., Inc., Rahway, N.J.

[21] Appl. No.: 08/836,863

[22] PCT Filed: Dec. 8, 1995

[86] PCT No.: PCT/US95/16158

§ 371 Date: May 22, 1997

§ 102(e) Date: May 22, 1997

[87] PCT Pub. No.: WO96/18617

PCT Pub. Date: Jun. 20, 1996

[51] Int. Cl.[6] .................. C07D 213/75; C07D 215/38; A61K 31/44; A61K 31/34

[52] U.S. Cl. ............... 514/252; 514/231.5; 514/253; 514/299; 514/300; 514/301; 514/310; 514/313; 514/353; 544/105; 544/360; 544/350; 546/112; 546/113; 546/114; 546/143; 546/159; 546/306

[58] Field of Search ................. 546/306, 112, 546/113, 114, 143, 159; 514/353, 231.5, 252, 253, 299, 300, 301, 310, 313; 544/105, 350, 360

[56] References Cited

FOREIGN PATENT DOCUMENTS

| WO 93/13055 | 7/1993 | WIPO . |
|---|---|---|
| WO 93/24126 | 12/1993 | WIPO . |
| WO 94/12163 | 6/1994 | WIPO . |
| WO 94/12165 | 6/1994 | WIPO . |
| WO 94/12645 | 6/1994 | WIPO . |
| WO 94/14780 | 7/1994 | WIPO . |
| WO 94/16729 | 8/1994 | WIPO . |
| WO 94/21621 | 9/1994 | WIPO . |
| WO 94/23038 | 10/1994 | WIPO . |
| WO 95/11231 | 4/1995 | WIPO ................... 546/305 |

OTHER PUBLICATIONS

W.M. Moore, et al., J. Med. Chem., 37, pp. 3886–3888 (1994).

E.P. Garvey, et al., Journal of Biological Chem., 269 No. 43, pp. 26669–26676 (1994).

Singh, Agric. Biol. Chem, vol. 42(6) pp. 1285–1286, 1978.

Vasilev et al, Fiziol. Rast. (Sofia). vol. 10(2) pp. 40–49, 1984.

Sarkis et al, I. Heterocycl. Chem, vol. 22(1), pp. 137–140, 1985.

*Primary Examiner*—Zinna Northington Davis
*Attorney, Agent, or Firm*—Richard C. Billups; David L. Rose; Curtis C. Panzer

[57] ABSTRACT

Substituted 2-acylaminopyridine compounds and pharmaceutically acceptable salts which have been found useful in the treatment of nitric oxide synthase mediated diseases and disorders.

6 Claims, No Drawings

SUBSTITUTED 2-ACYLAMINO-PYRIDINES AS INHIBITORS OF NITRIC OXIDE SYNTHASE

This application is a 371 of PCT/US 95/16158 filed Dec. 8, 1995.

BACKGROUND OF THE INVENTION

This application is directed to inhibitors of nitric oxide synthase, and in particular 2-acylamino-pyridines.

Nitric Oxide in Biology

The emergence of nitric oxide (NO), a reactive, inorganic radical gas as a molecule contributing to important physiological and pathological processes is one of the major biological revelations of recent times. This molecule is produced under a variety of physiological and pathological conditions by cells mediating vital biological functions. Examples include endothelial cells lining the blood vessels; nitric oxide derived from these cells relaxes smooth muscle and regulates blood pressure and has significant effects on the function of circulating blood cells such as platelets and neutrophils as well as on smooth muscle, both of the blood vessels and also of other organs such as the airways. In the brain and elsewhere nitric oxide serves as a neurotransmitter in non-adrenergic non-cholinergic neurons. In these instances nitric oxide appears to be produced in small amounts on an intermittent basis in response to various endogenous molecular signals. In the immune system nitric oxide can be synthesized in much larger amounts on a protracted basis. Its production is induced by exogenous or endogenous inflammatory stimuli, notably endotoxin and cytokines elaborated by cells of the host defense system in response to infectious and inflammatory stimuli. This induced production results in prolonged nitric oxide release which contributes both to host defense processes such as the killing of bacteria and viruses as well as pathology associated with acute and chronic inflammation in a wide variety of diseases. The discovery that nitric oxide production is mediated by a unique series of three closely related enzymes, named nitric oxide synthases, which utilize the amino acid arginine and molecular oxygen as co-substrates has provided an understanding of the biochemistry of this molecule and provides distinct pharmacological targets for the inhibition of the synthesis of this mediator, which should provide significant beneficial effects in a wide variety of diseases.

Nitric Oxide Synthases

Nitric oxide and L-citrulline are formed from L-arginine via the dioxygenase activity of specific nitric oxide synthases (NOSs) in mammalian cells. In this reaction, L-arginine, $O_2$ and NADPH are co-substrates while FMN, FAD and tetrahydrobiopterin are co-factors. NOSs fall into two distinct classes, constitutive NOS (cNOS) and inducible NOS (iNOS). Two constitutive NOSs have been identified. They are:

(i) a constitutive, $Ca^{++}$/calmodulin dependent enzyme, located in the endothelium (ecNOS or NOS 3), that releases NO in response to receptor or physical stimulation, (ii) a constitutive, $Ca^{++}$/calmodulin dependent enzyme, located in the brain (ncNOS or NOS 1) and elsewhere, that releases NO in response to receptor or physical stimulation, The third isoform identified is inducible NOS (iNOS or NOS 2):

(iii) a $Ca^{++}$ independent enzyme which is induced after activation of vascular smooth muscle, macrophages, endothelial cells, and a large number of other cells by endotoxin and cytokines. Once expressed, this inducible NO synthase produces NO in relatively large amounts for long periods of time.

Spectral studies of both the mouse macrophage iNOS and rat brain ncNOS have shown that these enzymes (which has been classified as P-450-like enzymes from their CO-difference spectra) contain a heme moiety. The structural similarity between NOS and the P-450-flavoprotein complex suggests that the NOS reaction mechanism may be similar to P-450 hydroxylation and/or peroxidation. This indicates that NOS belongs to a class of flavohemeproteins which contain both heme and flavin binding regions within a single protein in contrast to the multiprotein NADPH oxidase or Cytochrome P-450/NADPH Cyt c reductase complexes.

Distinct Functions of NO Produced by Different Nitric Oxide Synthases

The NO released by the constitutive enzymes (NOS 1 and NOS 3) acts as an autocoid mediating a number of physiological responses. Two distinct cDNAs accounting for the activity of NOS 1 and NOS 3 in man have been cloned, one for NOS 1 (Nakane et al., *FEBS Letters,* 316, 175–182, 1993) which is present in the brain and a number of peripheral tissues, the other for an enzyme present in endothelium (NOS 3) (Marsden et al., *FEBS Letters,* 307, 287–293, 1992). This latter enzyme is critical for production of NO to maintain vasorelaxation. A second class of enzyme, iNOS or NOS 2, has been cloned from human liver (Geller et aL, *PNAS,* 90, 3491–5, 1993), and identified in more than a dozen other cells and tissues, including smooth muscle cells, chondrocytes, the kidney and airways. As with its counterpart from the murine macrophage, this enzyme is induced upon exposure to cytokines such as gamma interferon (IFN-γ), interleukin- 1β (IL-1β), tumor necrosis factor (TNF-α) and LPS (lipopolysaccharide). Once induced, iNOS expression continues over a prolonged period of time. The enzyme does not require exogenous calmodulin for activity.

Endothelium derived relaxation factor (EDRF) has been shown to be produced by NOS 3 (Moncada et al., *Pharmacol. Reviews,* 43, 109–142, 1991). Studies with substrate analog inhibitors of NOS have shown a role for NO in regulating blood pressure in animals and blood flow in man, a function attributed to NOS 3. NO has also been shown to be an effector of the cytotoxic effects of activated macrophages (Nathan, *FASEB J.,* 6, 3051–64, 1992) for fighting tumour cells and invading microorganisms (Wright et al., *Card. Res.,* 26,48–57, 1992 and Moncada et al., *Pharmacological Review,* 43, 109–142, 1991). It also appears that the adverse effects of excess NO production, in particular pathological vasodilation and tissue damage, may result largely from the effects of NO synthesized by the NOS 2.

NO generated by NOS 2 has been implicated in the pathogenesis of inflammatory diseases. In experimental animals hypotension induced by LPS or TNF-α can be reversed by NOS inhibitors and reinitiated by L-arginine (Kilbourn et al., *PNAS,* 87, 3629–32, 1990). Conditions which lead to cytokine-induced hypotension include septic shock, hemodialysis (Beasley and Brenner, *Kidney Int.,* 42, Suppl., 38, S96–S100, 1992) and IL-2 therapy in cancer patients (Hibbs et al., *J. Clin. Invest.*, 89, 867–77, 1992). NOS 2 is implicated in these responses, and thus the possibility exists that a NOS inhibitor would be effective in ameliorating cytokine-induced hypotension. Recent studies in animal models have suggested a role for NO in the pathogenesis of inflammation and pain and NOS inhibitors have been shown to have beneficial effects on some aspects of the inflammation and tissue changes seen in models of inflammatory bowel disease, (Miller et al., *J. Pharmacol. Exp. Ther.*, 264, 11–16, 1990) and cerebral ischemia and arthritis (Ialenti et al., *Br. J. Pharmacol.*, 110, 701–6, 1993; Stevanovic-Racic et al., *Arth. & Rheum.*, 37, 1062–9, 1994). Moreover transgenic mice deficient in NOS 1 show diminished cerebral ischemia (Huang et al., *Science*, 265, 1883–5, 1994).

Further conditions where there is an advantage in inhibiting NO production from L-arginine include therapy with cytokines such as TNF, IL-1 and IL-2 or therapy with cytokine-inducing agents, for example 5,6-dimethylxanthenone acetic acid, and as an adjuvant to short term immunosuppression in transplant therapy. In addition, compounds which inhibit NO synthesis may be of use in reducing the NO concentration in patients suffering from inflammatory conditions in which an excess of NO contributes to the pathophysiology of the condition, for example adult respiratory distress syndrome (ARDS) and myocarditis.

There is also evidence that an NO synthase enzyme may be involved in the degeneration of cartilage which takes place in autoimmune and/or inflammatory conditions such as arthritis, rheumatoid arthritis, chronic bowel disease and systemic lupus erythematosis (SLE). It is also thought that an NO synthase enzyme may be involved in insulin-dependent diabetes mellitus. Therefore, a yet further aspect of the present invention provides cyclic amidine derivatives or salts thereof in the manufacture of a medicament for use in cytokine or cytokine-inducing therapy, as an adjuvant to short term immunosuppression in transplant therapy, for the treatment of patients suffering from inflammatory conditions in which an excess of NO contributes to the pathophysiology of the condition.

SUMMARY OF THE INVENTION

The invention disclosed herein encompasses compounds of Formula (I)

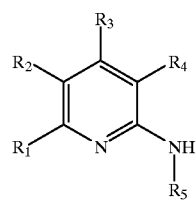

(I)

and pharmaceutically acceptable salts thereof which have been found to be useful in the treatment of nitric oxide synthase-mediated diseases and disorders, including neurodegenerative disorders, disorders of gastrointestinal motility and inflammation. These diseases and disorders include hypotension, septic shock, toxic shock syndrome, hemodialysis, IL-2 therapy such as in cancer patients, cachexia, immunosuppression such as in transplant therapy, autoimmune and/or inflammatory indications including sunburn, eczema or psoriasis and respiratory conditions such as bronchitis, asthma, oxidant-induced lung injury and acute respiratory distress (ARDS), glomerulonephritis, inflammatory sequelae of viral infections, myocarditis, heart failure, atherosclerosis, arthritis, rheumatoid arthritis, chronic or inflammatory bowel disease, ulcerative colitis, Crohn's disease, systemic lupus erythematosis (SLE), ocular conditions such as ocular hypertension, retinitis and uveitis, type 1 diabetes, insulin-dependent diabetes mellitus and cystic fibrosis. Compounds of Formula I are also useful in the treatment of hypoxia, hyperbaric oxygen convulsions and toxicity, dementia, Sydenham's chorea, Parkinson's disease, Huntington's disease, amyotrophic lateral sclerosis, mulitple sclerosis, Korsakoff's disease, imbecility related to cerebral vessel disorder, NO mediated cerebral trauma and related sequelae, ischemic brain edema, sleeping disorders, schizophrenia, depression, pre-menstrual syndrome (PMS), anxiety, drug addiction, pain, migraine, immune complex disease, as immunosupressive agents, acute allograft rejection, infections caused by invasive microorganisms which produce NO, radiocontrast induced renal failure and for preventing or reversing tolerance to opiates and diazepines.

DETAILED DESCRIPTION OF THE INVENTION

The invention disclosed herein encompasses compounds of Formula (I)

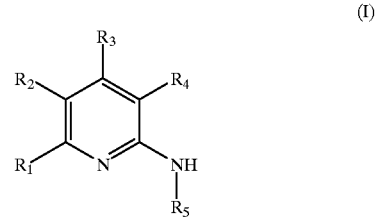

(I)

or a pharmaceutically acceptable salt thereof wherein:
$R_1$, $R_2$, $R_3$ and R4 are each independently selected from the group consisting of
(a) hydrogen,
(b) hydroxy,
(c) amino,
(d) carboxyl,
(e) aminocarbonyl,
(f) cyano,
(g) nitro,
(h) halo, where halo is selected from fluoro, chloro, bromo, and iodo,
(i) trifluoromethyl,
(j) $C_{1-12}$alkyl,
(k) $C_{2-12}$alkenyl,
(l) $C_{2-12}$alkynyl,
(m) $C_{1-12}$alkoxy,
(n) $C_{1-12}$alkylcarbonyl,
(o) $C_{1-12}$alkoxycarbonyl,
(p) $C_{1-12}$alkylaminocarbonyl,
(q) mono- and di-$C_{1-12}$alkylamino,
(r) $C_{1-12}$alkylthio,
(s) aryl, where aryl is selected from phenyl and naphthyl,
(t) aryloxy, where aryl is selected from phenyl and naphthyl,
(u) arylthio, where aryl is selected from phenyl and naphthyl,
(v) aryl$C_{1-6}$alkyl, where aryl is selected from phenyl and naphthyl, (w) cycloalkyl, wherein the cycloalkyl is a 5- to 10-membered monocyclic ring which optionally contains 1 or 2 heteroatoms selected from S, O, and N,
(x) heteroaryl, wherein heteroaryl is selected from the group consisting of:
(1) pyridyl,
(2) pyrrolyl,
(3) furanyl,
(4) thienyl,
(5) isothiazolyl,
(6) imidazolyl,
(7) benzimidazolyl,
(8) tetrazolyl,
(9) pyrazinyl,
(10) pyrimidyl,
(11) quinolyl,
(12) isoquinolyl,
(13) benzofuranyl,
(14) isobenzofuryl,
(15) benzothienyl,
(16) pyrazolyl,
(17) pyrazinyl
(18) indolyl,
(19) isoindolyl,
(20) purinyl,
(21) carbazolyl,
(22) isoxazolyl,
(23) thiazolyl,
(24) triazolyl
(25) oxazolyl,
(26) oxadiazolyl,
(27) thiadiazolyl
(28) benzthiazolyl, and
(29) benzoxazolyl,
(y) heteroaryl$C_{1-6}$alkyl, where heteroaryl is defined above in item (x), each of (j) to (y) being optionally mono- or di- substituted, the substituents being independently selected from
(1) hydroxy,
(2) $C_{1-6}$alkyl,
(3) $C_{1-6}$alkoxy,
(4) amino,
(5) mono- and di-$C_{1-6}$alkylamino,
(6) carboxyl,
(7) $C_{1-6}$alkylthio,
(8) $C_{1-6}$alkyl-S(O)$_k$—, where k is 1 or 2,
(9) $C_{1-6}$alkoxycarbonyl,
(10) halo selected from fluoro, chloro, bromo, and iodo,
(11) oxo,
(12) amidino,
(13) guanidino, $R_1$ and $R_2$, or $R_2$ and $R_3$ or $R_3$ and $R_4$ including the optional substituents present thereon may be joined together to form a 5- to 10-membered saturated or unsaturated ring containing 0, 1 or 2 heteroatoms which together with the atoms to which $R_1$ and $R_2$, or $R_2$ and $R_3$ or $R_3$ and $R_4$ are attached there is formed a bicyclic ring according to Formulae (IIa-IIc), the heteroatoms being selected from the group consisting of O, S and N,

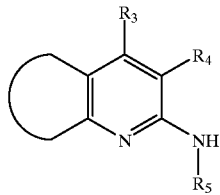

(IIa)

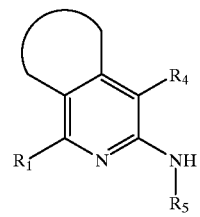

(IIb)

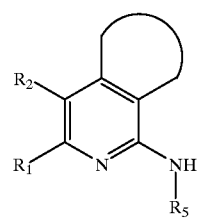

(IIc)

$R_5$ is selected from the group consisting of
(a) amino-C(=S)—,
(b) $C_{1-12}$alkylcarbonyl,
(c) $C_{2-12}$alkenylcarbonyl,
(d) $C_{2-12}$alkynylcarbonyl,
(e) $C_{5-10}$cycloalkylcarbonyl,
(f) arylcarbonyl, wherein the aryl group is selected from phenyl and naphthyl,
(g) heteroarylcarbonyl, wherein heteroaryl is selected from the group consisting of:
(1) pyridyl,
(2) pyrrolyl,
(3) furanyl,
(4) thienyl,
(5) isothiazolyl,
(6) imidazolyl,
(7) benzimidazolyl,
(8) tetrazolyl,
(9) pyrazinyl,
(10) pyrimidyl,
(11) quinolyl,
(12) isoquinolyl,
(13) benzofuranyl,
(14) isobenzofuryl,
(15) benzothienyl,
(16) pyrazolyl,
(17) pyrazinyl
(18) indolyl,
(19) isoindolyl,
(20) purinyl,
(21) carbazolyl,
(22) isoxazolyl,
(23) thiazolyl,
(24) triazolyl
(25) oxazolyl,
(26) oxadiazolyl,
(27) thiadiazolyl

(28) benzthiazolyl, and
(29) benzoxazolyl,
(h) $C_{1-12}$alkoxycarbonyl,
(i) aryloxycarbonyl, wherein the aryl group is selected from phenyl and naphthyl,
(j) heteroaryloxycarbonyl, wherein the heteroaryl group is defined as above in item (g),
(k) aryl$C_{1-6}$alkoxycarbonyl, wherein the aryl group is phenyl and naphthyl,
(l) heteroaryl$C_{1-6}$alkoxycarbonyl, wherein the heteroaryl group is defined as above in item (g),
(m) $C_{1-12}$alkylaminocarbonyl,
(n) $C_{1-12}$alkylaminosulfonyl,
(o) arylaminocarbonyl, wherein the aryl group is selected from phenyl and naphthyl,
(p) arylaminosulfonyl, wherein the aryl group is selected from phenyl and naphthyl,
(q) heteroarylaminocarbonyl, wherein the heteroaryl group is defined as above in item (g),
(r) heteroarylaminosulfonyl, wherein the heteroaryl group is defined above in item (g),
(s) $C_{1-12}$alkylamino-C(=S)—,
(t) $C_{2-12}$alkenylamino-C(=S)—,
(u) arylamino-C(=S)—, wherein the aryl group is selected from phenyl and naphthyl,
(v) aryl$C_{1-6}$alkylamino-C(=S)—, wherein the aryl group is selected from phenyl and naphthyl,
(w) heteroarylamino-C(=S)—, wherein the heteroaryl group is defined above in item (g),
(x) heteroaryl$C_{1-6}$alkylamino-C(=S)—, wherein the heteroaryl group is defined above in item (g),
(y) cyclo$C_{5-10}$alkylamino-C(=S)—,
(z) aryl-C—(=O)—NH—C(=O)—, wherein the aryl group is selected from phenyl and naphthyl,
(aa) heteroaryl-C(=O)—NH—C(=O)—, wherein the heteroaryl group is defined above in item (g),
(ab) $R_6R_7N$—$SO_2$—NH—C(=O)—, wherein $R_6$ and $R_7$ are independently selected from the group consisting of
  (1) hydrogen,
  (2) $C_{1-6}$alkyl,
  (3) aryl, wherein the aryl group is selected from phenyl and naphthyl,
  (4) heteroaryl, wherein the aryl group is selected from the group pyridyl, thienyl, thiazolyl, isothiazolyl, imidazolyl, and triazolyl,
  (5) $R_6$ and $R_7$ may be joined together to form a 5- to 10-membered monocylic ring containing 0, 1 or 2 heteroatoms, the heteroatoms being selected from the group of S, O, and N,
each of (b) to (ab) being optionally mono- or di-substituted, the substituents being independently selected from
(1) hydroxy,
(2) $C_{1-6}$alkyl,
(3) $C_{1-6}$alkoxy,
(4) amino,
(5) mono- and di-$C_{1-6}$alkylamino,
(6) carboxyl,
(7) $C_{1-6}$alkylthio,
(8) $C_{1-6}$alkyl-$S(O)_k$—, where k is 1 or 2,
(9) $C_{1-6}$alkoxycarbonyl,
(10) halo selected from fluoro, chloro, bromo, and iodo,
(11) oxo,
(12) amidino,
(13) guanidino Within this embodiment there is the genus of compounds wherein
$R_1$, $R_2$, $R_3$ and $R_4$ are each independently selected from the group consisting of
(a) hydrogen,
(b) hydroxy,
(c) amino,
(d) cyano,
(e) fluoro, chloro, bromo, and iodo,
(f) trifluoromethyl,
(g) $C_{1-6}$alkyl,
(h) $C_{1-6}$alkoxy,
(i) $C_{1-6}$alkylthio,
(j) $C_{1-6}$alkylcarbonyl,
(k) mono- and di-$C_{1-6}$alkylammo,
(l) aryl, where aryl is phenyl and naphthyl,
(m) aryloxy, where aryl is phenyl and naphthyl,
(n) cycloalkyl, wherein the cycloalkyl is a 5-, 6-, or 7-membered monocyclic ring which optionally contains 1 or 2 heteroatoms selected from S, O, and N,
(o) heteroaryl, wherein heteroaryl is selected from the group consisting of:
  (1) pyridyl,
  (2) furanyl,
  (3) thienyl,
  (4) pyrazinyl,
  (5) pyrimidyl,
  (6) thiazolyl, and
  (7) triazolyl,
each of (g) to (o) being optionally mono- or di-substituted, the substituents being independently selected from
(1) hydroxy,
(2) $C_{1-4}$alkyl,
(3) $C_{1-3}$alkoxy,
(4) amino,
(5) mono- and di-$C_{-6}$alkylamino,
(6) carboxyl,
(7) $C_{1-3}$alkylthio,
(8) $C_{1-3}$alkyl-$S(O)_k$—, where k is 1 or 2,
(9) $C_{1-4}$alkoxycarbonyl,
(10) halo selected from fluoro, chloro, bromo, and iodo,
(11) oxo,
(12) amidino, $R_1$ and $R_2$, or $R_2$ and $R_3$ or $R_3$ and $R_4$ including the optional substituents present thereon may be joined together to form a 5-, 6- or 7-membered saturated monocyclic ring containing 0, 1 or 2 heteroatoms which together with the atoms to which $R_1$ and $R_2$, or $R_2$ and $R_3$ or $R_3$ and $R_4$ are attached there is formed a bicyclic ring according to Formulae (IIa–IIc), the heteroatoms being selected from the group consisting of O, S and N,

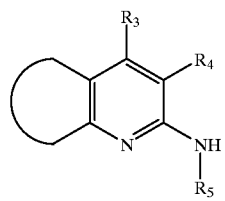
(IIa)

-continued

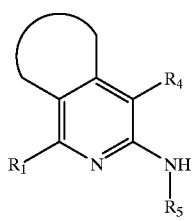

(IIb)

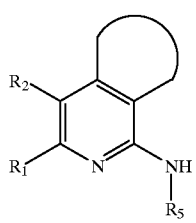

(IIc)

$R_5$ is selected from the group consisting of
(a) amino-C(=S)—,
(b) $C_{1-6}$alkylcarbonyl,
(c) aroyl, wherein the aroyl group is benzoyl,
(d) $C_{1-6}$alkylamino-C(=S)—,
(e) $C_{2-6}$alkenylamino-C(=S)—,
(f) arylarnino-C(=S)—, wherein the aryl group is phenyl and naphthyl
(g) arylC1–6alkylamino-C(=S)', wherein the aryl group is phenyl and naphthyl,
(h) cyclo$C_{5-7}$alkylamino-C(=S)—,
(i) aroylaminocarbonyl, wherein the aroyl group is benzoyl and naphthoyl,
(j) $R_6R_7N$—$SO_2$—NH—C(=O)—, wherein $R_6$ and $R_7$ are independently selected from the group consisting of
  (1) hydrogen,
  (2) $C_{1-6}$alkyl
  (3) aryl, wherein the aryl group is selected from phenyl,
  (4) $R_6$ and $R_7$ may be joined together to form a 5 5-, 6- or 7-membered ring containing 0 to 2 heteroatoms, the heteroatoms being elected from the group of oxygen, sulfur and nitrogen,
each of (b) to (j) being optionally mono- or di- substituted, the substituents being independently selected from
  (1) hydroxy,
  (2) $C_{1-4}$alkyl,
  (3) $C_{1-3}$alkoxy,
  (4) amino,
  (5) mono- and di-$C_{1-6}$alkylamino,
  (6) carboxyl,
  (7) $C_{1-3}$alkylthio,
  (8) $C_{1-3}$alkyl-S(O)$_k$—, where k is 1 or 2,
  (9) $C_{1-4}$alkoxycarbonyl,
  (10) halo selected from fluoro, chloro, bromo, and iodo,
  (11) oxo,
  (12) amidino.
Within this genus there is a class of compounds wherein $R_1$, $R_2$, $R_3$ and $R_4$ are each independently selected from the group consisting of
(a) hydrogen,
(b) hydroxy,
(c) amino,
(d) cyano,
(e) fluoro, chloro or bromo,
(f) trifluoromethyl,
(g) $C_{1-4}$aLkyl,
(h) $C_{1-4}$alkoxy,
(i) $C_{1-4}$alkylthio,
(j) mono- and di-$C_{1-4}$alkylamino,
$R_1$ and $R_2$, or $R_2$ and $R_3$ or $R_3$ and $R_4$ including the optional substituents present thereon may be joined together to form a 5, 6 or 7-membered unsaturated monocyclic ring containing 0, 1 or 2 heteroatoms which together with the atoms to which $R_1$ and $R_2$, or $R_2$ and $R_3$ or $R_3$ and $R_4$ are attached there is formed a bicyclic ring according to Formulae (IIa–IIc), the heteroatoms being selected from the group consisting of O, S and N,

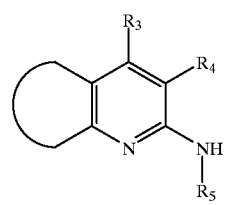

(IIa)

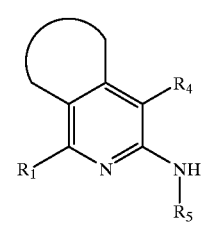

(IIb)

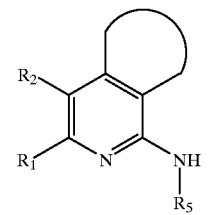

(IIc)

$R_5$ is selected from the group consisting of
(a) amino-C(=S)—,
(b) $C_{1-4}$alkylamino-C(=S)—,
(c) $C_{2-4}$alkenylamino-C(=S)—,
(d) arylamino-C(=S)—, wherein the aryl group is phenyl and naphthyl,
(e) arylC1–4alkylamino-C(=S)—, wherein the aryl group is phenyl,
(f) $R_6R_7N$—$SO_2$—NH—C(=O)—, wherein $R_6$ and $R_7$ are independently selected from the group consisting of
  (1) hydrogen,
  (2) $C_{1-4}$alkyl
  (3) aryl, wherein the aryl group is selected from phenyl,
each of (b) to (f) being optionally mono- or di- substituted, the substituents being independently selected from
  (1) hydroxy,
  (2) $C_{1-4}$alkyl, (3) $C_{1-3}$alkoxy,
(4) amino,
(5) mono- and di-$C_{1-6}$alkylamino,
(6) carboxyl,
(7) $C_{1-3}$alkylthio,
(8) halo selected from fluoro, chloro, and bromo.

Within this class are compounds wherein the rings of Formulae IIa, IIb and IIc are selected from the group consisting of

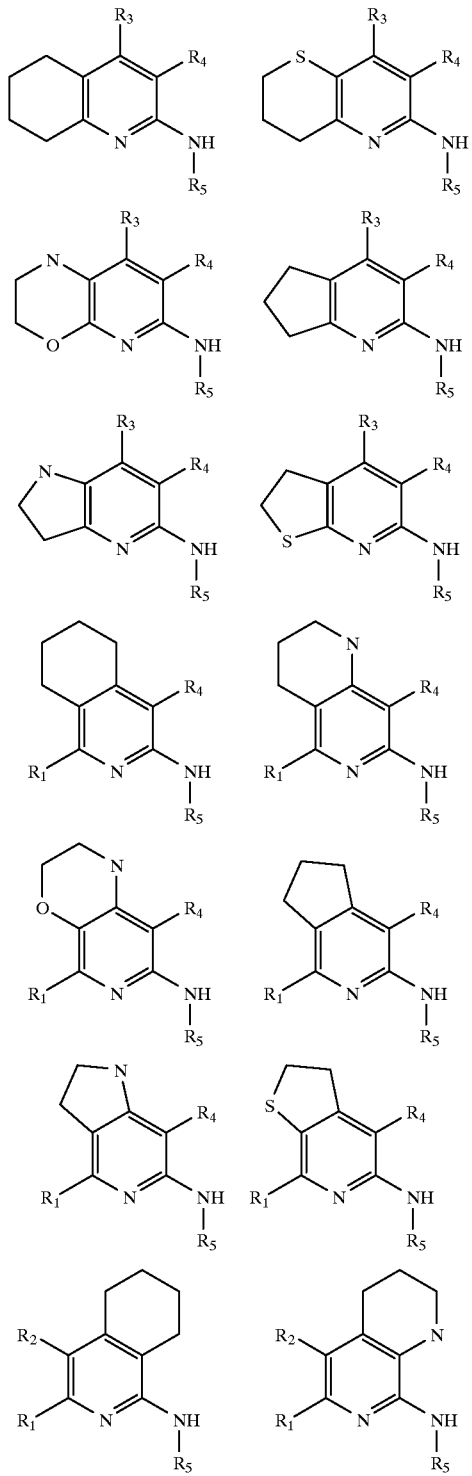

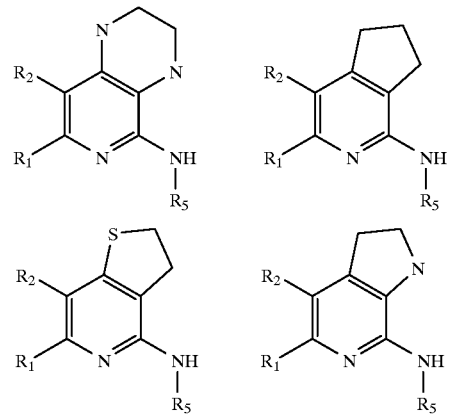

Within the above genus of compounds of Formulae IIa, IIb and IIc where $R_1$, $R_2$, $R_3$ or $R_4$ is not explicitly joined into a ring, then $R_1$, $R_2$, $R_3$ and $R_4$ are each independently selected from the group consisting of
(a) hydrogen,
(b) hydroxy,
(c) amino,
(d) cyano,
(e) fluoro, chloro or bromo,
(f) trifluoromethyl,
(g) $C_{1-4}$alkyl,
(h) $C_{1-4}$alkoxy,
(i) $C_{1-4}$alkylthio,
(j) mono- and di-$C_{1-4}$alkylamino, $R_5$ is selected from the group consisting of
(a) amino-C(=S)—,
(b) $C_{1-4}$alkylamino-C(=S)—,
(c) $C_{2-4}$alkenylarnino-C(=S)—,
(d) arylamino-C(=S)—, wherein the aryl group is phenyl and naphthyl,
(e) arylC1–4alkylamino-C(=S)—, wherein the aryl group is phenyl,
(f) $R_6R_7N$—$SO_2$—NH—C(=O)—, wherein $R_6$ and $R_7$ are independently selected from the group consisting of
    (1) hydrogen,
    (2) $C_{1-4}$alkyl
    (3) aryl, wherein the aryl group is selected from phenyl, each of (b) to (f) being optionally mono- or di-substituted, the substituents being independently selected from
(1) hydroxy,
(2) $C_{1-4}$alkyl,
(3) $C_{1-3}$alkoxy,
(4) amino,
(5) mono- and di-$C_{1-6}$alkylamino,
(6) carboxyl,
(7) $C_{1-3}$alkylthio,
(8) halo selected from fluoro, chloro, and bromo.

Illustrating the invention are the compounds provided in Table 1.

For purposes of this specification alkyl is defmed to include linear, branched, and cyclic structures, with $C_{1-6}$alkyl including methyl, ethyl, propyl, 2-propyl, s- and t-butyl, butyl, pentyl, hexyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like. Likewise, $C_{1-6}$ aLkylthio is intended to include alkylthio groups of from 1 to 6 carbon atoms of a straight, branched or cyclic configuration. Examples of lower alkylthio groups include methylthio, propylthio, isopropylthio, cycloheptylthio, etc. By way of illustration, the propylthio group signifies —$SCH_2CH_2CH_3$.

Heteroaryl includes but is not limited to, pyridyl, pyrrolyl, furanyl, thienyl, isothiazolyl, imidazolyl, benzimidazolyl, tetrazolyl, pyrazinyl, pyrimidyl, quinolyl, isoquinolyl, benzofuranyl, isobenzofuryl, benzothienyl, pyrazolyl, pyridazinyl, indolyl, isoindolyl, purinyl, carboxazolyl, isoxazolyl, thiazolyl, triazolyl, oxazolyl, oxadiazolyl, thiadiazolyl, benzthiazolyl and benzoxazolyl.

As outlined in the summary of the invention, the compounds of the instant invention are useful for in the treatment of a number of NOS implicated diseases. The implication of these diseases is well documented in the literature. For example, with regard to psoriasis, see Ruzicka et al., J. Invest. Derm., 103: 397 (1994) or Kolb-Bachofen et al., Lancet, 344: 139 (1994) or Bull, et al., *J. Invest. Derm.,* 103:435(1994); with regard to uveitis, see Mandia et al., Invest Opthalmol., 35: 3673–89 (1994); with regard to type 1 diabetes, see Eisieik & Leijersfam, Diabetes & Metabolism, 20: 116–22 (1994) or Kroncke et al., BBR C, 175: 752–8 (1991) or Welsh et al., *Endocrinol.,* 129: 3167–73 (1991); with regard to septic shock, see Petros et al., Lancet, 338: 1557–8 (1991),Thiemermann & Vane, Eur. J. Phannacol., 211: 172–82 (1992), or Evans et al., Infec. Imm., 60: 4133–9 (1992), or Schilling et al., Intensive Care Med., 19: 227–231 (1993); with regards to pain, see Moore et al, Brit. J. Pharmacol., 102: 198–202 (1991), or Moore et al, Brit. J. Pharmacol., 108: 296–97 (1992) or Meller et al., *Europ. J. Phannacol.,* 214: 93–6 (1992) or Lee et al., *NeuroReport,* 3: 841–4 (1992); with regard to migraine, see Olesen et aL, TIPS, 15: 149–153 (1994); with regard to rheumatoid arthritis, see Kaurs & Halliwell, FEBS Letters, 350: 9–12 (1994); with regard to osteoarthritis, see Stadler et aL, *J. Immunol.,* 147: 3915–20 (1991); with regard to inflammatory bowel disease, see Miller et al., Lancet, 34: 465–66 (1993) or Miller et al., J. Pharmacol. Exp. Ther., 264: 11–16 (1993); with regard to asthma, see Hamid et al., Lancet, 342: 1510–13 (1993) or Kharitonov, et aL, Lancet, 343: 133–5 (1994); with regard to Immune complex diseases, see Mulligan et al., Br. J. Pharmacol., 107: 1159–62 (1992); with regard to multiple sclerosis, see Koprowski et al., *PNAS,* 90: 3024–7 (1993); with regard to ischemic brain edema, see Nagafuji et al., Neurosci., 147: 159–62 (1992) or Buisson et al., Br. J. Pharmacol., 106: 766–67 (1992) or Trifiletti et al., *Europ. J. Phannacol.,* 218: 197–8 (1992); with regard to toxic shock syndrome, see Zembowicz & Vane, PNAS, 89: 2051–55 (1992); with regard to heart failure, see Winlaw et al., Lancet, 344: 373–4 (1994); with regard to ulcerative colitis, see Boughton-Smith et aL, Lancet 342: 338–40 (1993); and with regard to atherosclerosis, see White et al., PNAS, 91: 1044–8 (1994); with regard to glomerulonephritis, see Mühl et al., *Br. J. Pharmcol,* 112: 1–8 (1994); with regard to paget's disease and osteoporosis, see Löwick et al., *J. Clin. Invest.,* 93: 1465–72 (1994); with regard to inflammatory sequelae of viral infections, see Koprowski et al., *PNAS,* 90: 3024–7 (1993); with regard to retinitis, see Goureau et al., *BBRC,* 186: 854–9 (1992); with regard to oxidant induced lung injury, see Berisha et al., *PNAS,* 91: 744–9 (1994); with regard to eczema, see Ruzica, et al., *J. Invest. Derm.,* 103:395(1994); with regard to acute allograft rejection, see Devlin, J. et al., *Transplantation,* 58:592–595 (1994); with regard to infection caused by invasive microorganisms which produce NO, see Chen, Y and Rosazza, J. P. N., *Biochem. Biophys. Res. Comm.,* 203:1251–1258(1994), and with regard to radiocontrast induced renal failure, see Schwaartz, et al., *Am. J. Physiol,* 267:F374–9 (1994).

It will be understood that in the discussion of methods of treatment which follows, references to the compounds of Formula I are meant to also include the pharmaceutically acceptable salts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethy-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Synthesis of 2-Aminopyridines

Several methods for preparing the compounds of this invention are illustrated in the following schemes and examples. Some of the compounds are known in the literature and are commercially available. Several reviews for the preparation of 2-aminopyridine derivatives have appeared (M. T. Leffler in *Organic Reactions*, Vol. 1, R. Adams, ed., J. Wiley and Sons, NY, 1942, Ch. 4, pp. 91–104; A. S. Tomcufcik and L. N., Starker in *The Chemistry of Heterocyclic Compounds, Pyridine and Its Derivatives, Part 3*, E. Klingsberg, ed.; Interscience, NY, 1962, Ch. IX, pp. 1–177; E. F. V. Scriven in *Comprehensive Heterocyclic Chemistry*, Vol. 2, Part 2A, A. J. Boulton and A. McKillop, eds., Pergamon Press, NY, 1984, Ch. 2.05, pp. 165–314).

In one method illustrated Scheme 1, these compounds are prepared by the Chitchibabin reaction involving the reaction of a substituted pyridine derivative with sodium amide or sodium amide in the presence of a substituted amine to yield a 2-aminopyridine derivative. This methodology is amenable to a broad range of substitutents. The pyridine and substituted amine starting materials are commercially available or they can be prepared by the methods known to those skilled in the art.

SCHEME 1

Chitchibabin Reaction

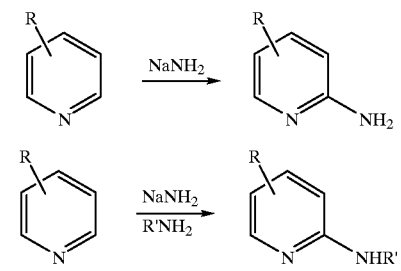

As shown in Scheme 2, the Hofmann rearrangement of a pyridyl-2-carboxamide in the presence of a hypohalite will give a 2-aminopyridine. Similarly, a Curtius rearrangement of a pyridyl-2-hydrazide will also give the desired derivative. Similarly, a Lossen rearrangement of a pyridyl-2- hydroxamic acid will also afford 2-aminopyridine. Similarly, treatment of a pyridyl-2-hydroxamate-O-sulfonic acid with acid gives 2-aminopyridine (Neber-type rearrangement). Picolinic acid starting materials are commercially available or they can be prepared by the methods known to those skilled in the art. [see E. P. Oliveto in *The Chemistry of Heterocyclic Compounds, Pyridine and Its Derivatives, Part* 3, E. Klingsberg, ed.; Interscience, NY, 1962, Ch. X, pp. 179–346.]

SCHEME 2

Hofmann Reaction

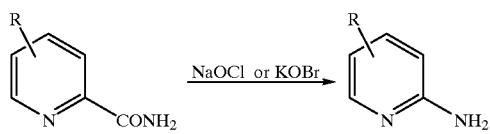

Curtius Reaction

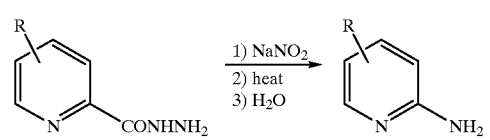

Modified Lossen Rearrangement

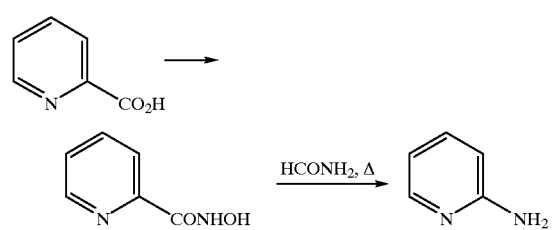

Neber-type rearrangement

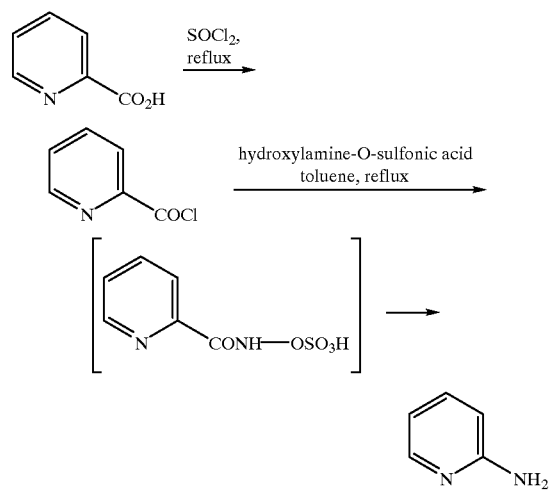

As outlined in Scheme 3, 2-halopyridines can be reacted with ammonia or substituted amines in the presence of copper (II) sulfate to form the 2-aminopyridine derivative. The preparation of a variety of 2-halopyridine derivatives has been reviewed (see H. E. Mertel in *The Chemistry of Heterocyclic Compounds, Pyridine and Its Derivatives, Part* 2 E. Klingsberg, ed.; Interscience, NY, 1962, Ch. VI, pp. 299–419). A recent publication describes new methodology for the preparation of highly finctionalized 2-halopyridine derivatives (see P. Rocca et al., *J. Org. Chem.* 1993, 58, 7832–7838).

Displacement of a 2-trifluoromethyl group with sodium amide in liquid ammonia also gives 2-aminopyridine.

SCHEME 3

2-Halogen Displacement (where X is a halogen)

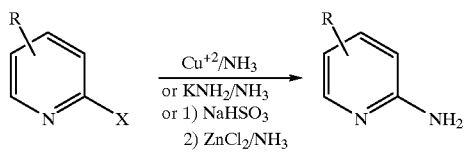

More recent methodology for the synthesis of 2-aminopyridine derivatives has recently been described (K. Wachi and A. Terada, *Chem. Pharm. Bull. Jap.*, 1980, 28, 465–472) and is outlined in Scheme 4. Pyridine-N-oxides can react with the imidoyl chloride of 1,3-benzoxazine to give N-(2-pyridyl)-1,3-benzoxazines. Subsequent treatment with strong acid affords the 2-aminopyridine.

SCHEME 4

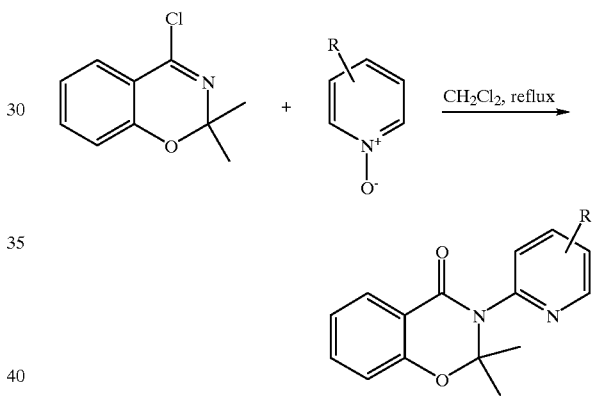

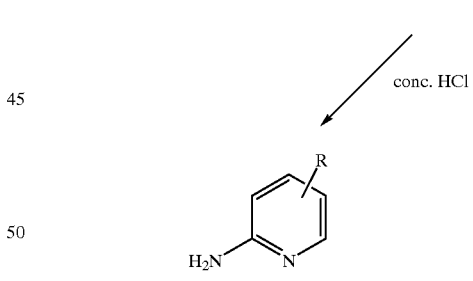

Methodology for the acylation of the 2-aminopyridines is outlined in Scheme 5. Briefly, an appropriately substituted 2-aminopyridine A is either a) reacted with an acid chloride derivative yield the amide B; or b) reacted with an isocyanate derivative to yield the urea C; or c) reacted first with thiophosgene followed by treatment with an amine to also yield the thiourea D; or d) reacted with an isothiocyanate derivative to yield the thiourea D. Other methodologies for the acylation of nitrogen have been described (See for example, *Advanced Organic Chemistry*, Thrid Ed, Jerry March, ed., John Wiley & Sons, pp 370 to 380) and can also be applied.

SCHEME 5

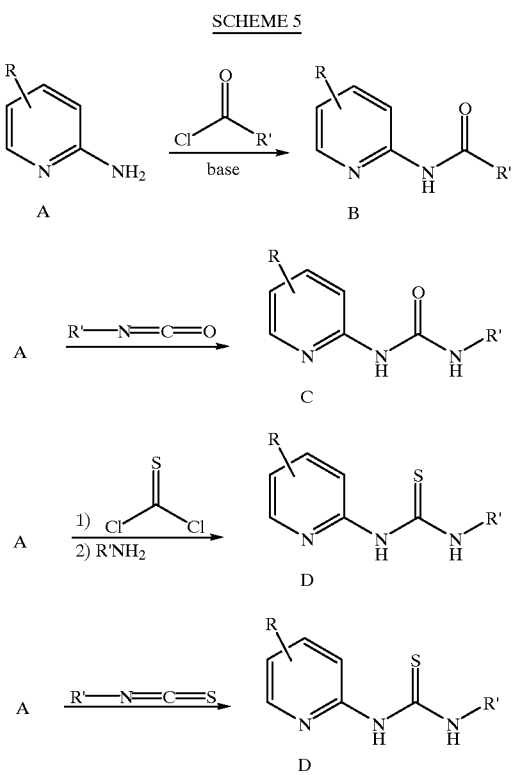

The N'-(aminosulfonyl)-ureas C were prepared following methodology described by Karady et al. in *Heterocycles*, 1979, 12, 815–818 and illustrated in Scheme 6. Thus, the appropriately substituted 2-aminopyridine A is reacted with chlorosulfonyl isocyanate in the presence of an organic base, such as triethylamine and diisopropylethylamine, to afford the intermediate thiatriazene B. Treatment of B with the appropriate R₆R₇NH amine, in a suitable solvent, such as acetonitrile, yields the desired N'-(aminosulfonyl)-urea C.

SCHEME 6

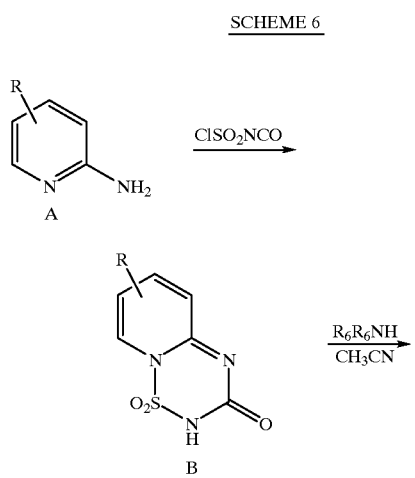

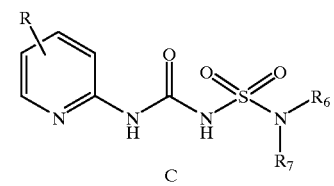

The invention will now be illustrated by the following non-limiting examples in which, unless stated otherwise:

all operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (δ) values for major diagnostic protons, given in parts per million (ppm) relative to tetramethylsilane (TMS) as internal standard, determined at 400 MHz or 500 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), niL (milliliters), g (gram(s)), mg (milligrams(s)), mol (moles), mmol (millimoles), eq (equivalent(s)).

EXAMPLE 1

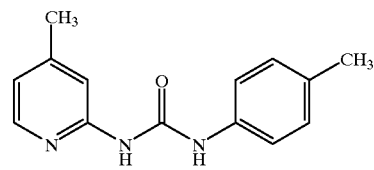

N-(2-(4-Methylpyridyl))-N'-(4-methylphenyl)-urea

A mixture of 2-amino-4-methylpyridine (108 mg; 1 mM) and 4-methylphenyl isocyanate (133 mg; 1 mM) in 5 mL of ether was stirred overnight at room temperature. The resulting white solid was filtered and washed twice with small amounts of ether. Drying the solid in vacuo resulted in 49 mg of the desired title compound.

¹H NMR (CDCl₃): 8.07 (d; J=5.5Hz; 1H); 7.47 (d; J=8.5 Hz; 2H); 7.12 (d; J=8.5 Hz; 2H); 6.75 (d; J=5.5 Hz; 1H); 6.72(s; 1H); 2.31(s; 3H); 2.32(s; 3H).

EXAMPLE 2

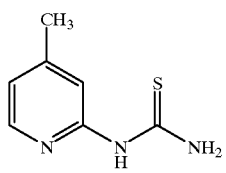

N-(2-(4-Methylpyridyl))-thiourea

To a stirred mixture of 2-amino-4-methylpyridine (505 mg) in chloroform (5 mL) and saturated sodium bicarbonate (5 mL) at 0° C. was added thiophosgene (1 eq., 0.36 mL). The reaction was gradually warmed to room temperature and stirred for 30 minutes. The two layers were separated and the aqueous layer successively extracted with chloroform (3×10 mL). The combined organic phases were successively washed with water (10 niL) and saturated salt solution (10 mL) and concentrated by rotoevaporation. The residue was dissolved in saturated methanolic ammonia (10 mL). After stirring at room temperature for 3 hr, the reaction mixture was concentrated by rotoevaporation. The crude product was purified by flash column chromatography on silica gel eluted with 30% ethyl acetate in hexanes to yield the desired product (0.14 gm).

$^1$H NMR (CDCl$_3$): 8.08, 8.05 (d, 1H), 7.9 (br s, 1H), 6.80, 6.68 (d, 1H), 2.3(s,3H).

EXAMPLE 3

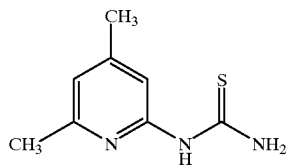

N-(2-(4,6-dimethylpyridyl))-thiourea

The title compound was synthesized according to the procedure in Example 2 by employing 2-amino-4,6-dimethylpyridine instead of 2-amino-4-methylpyridine.

$^1$H NMR (500 MHz, DMSO) : δ 10.70 (brs, 1H), 10.33 (brs, 1H), 8.76 (brs, 1H), 6.75 (s, 1H), 6.70 (s, 1H), 2.32 (s, 3H), 2.19 (s, 3H).

$^{13}$C NMR (DMSO) 181.04, 154.86, 153.66, 150.16, 118.71, 109.99, 23.89, 21.09 ppm.

EXAMPLE 4

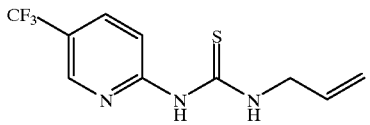

N-(2-(5-trifluoromethylpyridyl))-N'-allyl-thiourea

2-Amino-5-trifluoromethylpyridine (3.0 gm, 18.5 mmol) was added to allyl isothiocyanate (1.20 mL, 18.5 mmol) and heated to 100° C. The reaction mixture turned solid after about 1 hour. The reaction was stopped after 6 hours and cooled. The solid was washed with hexanes, filtered and dried under vacuum to yield the title compound (3.29 g).

$^1$H NMR (500 MHz, CDCl$_3$): δ 11.65 (brs, 1H), 9.88 (brs, 1H), 8.48 (s, 1H), 7.85 (dd, 1H), 7.1 l(d, 1H), 6.02 (m, 1H), 5.35–5.24 (m, 2H), 4.43 (m, 2H).

$^{13}$C NMR (CDCl$_3$) 179.61, 155.31, 143.61, 135.66, 116.88, 112.13, 47.97 ppm.

EXAMPLE 5

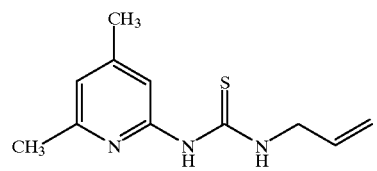

N-(2-(4,6-dimethylpyridyl))-N'-allyl-thiourea

The title compound was synthesized according to the procedure in Example 4 by employing 2-amino-4,6-dimethylpyridine instead of 2-amino-5-trifluoromethylpyridine.

$^1$H NMR (500 MHz, CDCl$_3$): δ 12.16 (brs, 1H), 9.07 (brs, 1H), 6.62 (s, 1H), 6.48 (s, 1H), 6.04 (m, 1H), 5.36–5.20 (m, 2H), 4.39 (m, 2H), 2.42 (s, 3H), 2.26 (s, 3H).

$^{13}$C NMR (CDCl$_3$): 179.65, 154.55, 153.05, 150.29, 133.28, 118.64, 109.15, 47.79, 23.63, 21.05 ppm.

EXAMPLE 6

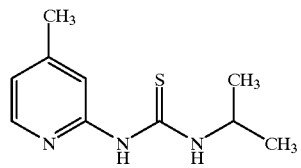

N-(2-(4-Methylpyridyl))-N'-isopropyl-thiourea

A mixture of 2-amino-4-methylpyridine (108 mg; 1 mmol) and isopropyl isothiocyanate (101 mg; 1 mmol) in benzene (5 mL) was heated to reflux for 1.5 days during which period all the solvent evaporated. The residue was purified by column chromatography on silica gel using 25% ethyl acetate in hexane to give the desired product as creamy solid.

$^1$H NMR (D$_6$-DMSO)): 8.07 (d; J=5.5 Hz; 1H); 6.95 (s; 1H); 6.86 (d; J=5.5Hz; 1H); 4.4 (m; 1H); 2.26 (s; 3H); 1.24 (d; 6H)

EXAMPLE 7

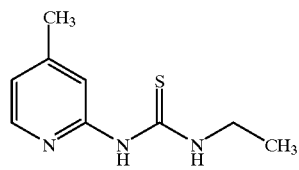

N-(2-(4-Methylpyridyl))-N'-ethyl-thiourea.

The title compound was synthesized according to the procedure in Example 6 by employing ethyl isothiocyanate instead of isopropyl isothiocyanate.

$^1$H NMR (D$_6$-DMSO)): 8.07 (d; J=5.5 Hz; 1H); 6.95 (s; 1H); 6.87 (d; J=5.5 Hz; 1H); 3.6 (q; 2H); 4.4 (m; 1H); 2.25 (s; 3H); 1.18 (t; 3H).

EXAMPLE 8

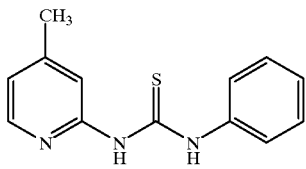

N-(2-(4-Methylpyridyl))-N'-phenyl-thiourea

A mixture of 2-amino-4-methylpyridine (108 mg, 1 mmol) and phenyl isothiocyanate (135 mg, 1 mmol) in ether (5 mL) was stirred at room temperature for 1 day. A solid separated and the supernatant was decanted. The solid was rinsed thoroughly with small amounts of ether (2x). The resulting white solid was dried in vacuo to give the desired product (52 mg).

$^1$H NMR (D$_6$-DMSO)): 8.17 (d; J=5 Hz; 1H); 7.18–7.7 (br m, 5H); 7.06 (s; 1H); 6.96(d; J=5 Hz; 1H); 2.3(s; 3H).

EXAMPLE 9

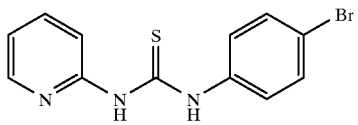

N-(2-Pyridyl)-N'-(4-bromophenyl)-thiourea

The title compound was synthesized according to the procedure in Example 8 by employing 4-bromophenyl isothiocyanate instead of phenyl isothiocyanate and 2-aminopyridine instead of 4-methyl-2-aminopyridine.

$^1$H NMR (CDCl$_3$): 8.33 (d; 1H); 7.85 (t; 1H); 7.7 (d; 2H); 7.57 (d; 2H); 7.23 (d; 1H); 7.16 (t; 1H).

EXAMPLE 10

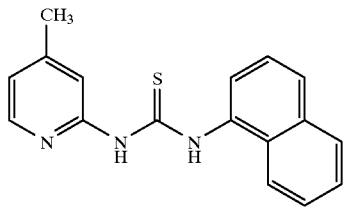

N-(2-(4-Methylpyridyl))-N'-(1-naphthyl)-thiourea

The title compound was synthesized according to the procedure in Example 8 by employing 1-naphthyl isothiocyanate instead of phenyl isothiocyanate.

$^1$H NMR (D$_6$-DMSO)): 8.18 (d; J=5 Hz; 1H); 7.52–8.02 (br m, 7H); 7.13(s; 1H); 6.99 (d; J=5 Hz; 1H); 2.32 (s; 3H).

EXAMPLE 11

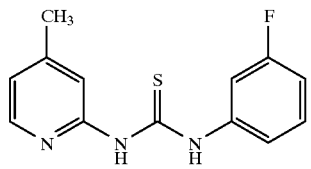

N-(2-(4-Methylpyridyl))-N'-(3-fluorophenyl)-thiourea

The title compound was synthesized according to the procedure in Example 8 by employing 3-fluorophenyl isothiocyanate instead of phenyl isothiocyanate.

$^1$H NMR (D$_6$-DMSO)): 8.2 (d; J=5.5 Hz; 1H); 7.0–7.92 (br m, 5H); 7.06 (s; 1H); 6.98 (d; J=5.5 Hz; 1H); 2.3(s; 3H).

EXAMPLE 12

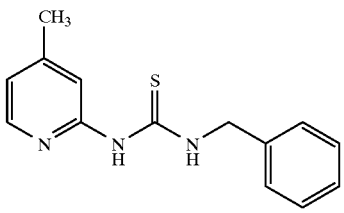

N-($^2$-($^4$-Methylpyridyl)-N'-benzyl-thiourea.

A mixture of $^2$-amino-4-methylpyridine (108 mg, 1 mmol), benzyl isothiocyanate (149 mg; 1 mmol) in toluene (2 mL) was heated to reflux for 3 days during which period the solvent evaporated. The residue was purified by column chromatography on silica gel using 25% of ethyl acetate in hexane to give the title compound (109 mg).

$^1$H NMR (D$_6$-DMSO)): 8.02 (d; J=5.5 Hz; 1H); 7.2–7.36 (br m, 5H); 6.98 (s; 1H); 6.87 (d; J=5.5 Hz; 1H); 4.9 (d; 2H); 2.26 (s; 3H)

EXAMPLE 13

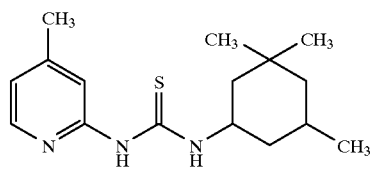

N-(2-(4-Methylpyridyl))-N'-(3,3,,5-trimethylcyclohexyl)-thiourea.

Mixture of 2-amino-4-methylpyridine (108 mg, 1 mmol) and 3,3,5-trimethyl cyclohexyl isothiocyanate (187 mg, mmol) in 2 mL of toluene was heated to reflux for 2 days. The solvent was removed and the residue was purified by column chromatography on silica gel using 25% ethyl acetate in hexane to provide the title compound (136 mg).

$^1$H NMR (D$_6$-DMSO)): 8.06 (d; J=5 Hz; 1H); 6.94(s, 1H); 6.86 d; J=5 Hz; 1H); 4.34 (m; 1H); 2.26 (s; 3H); 0.72–2.1 (br m, 7H); 0.88 (d; 3H); 0.92 (s, 3H), 0.93 (s; 3H).

EXAMPLE 14

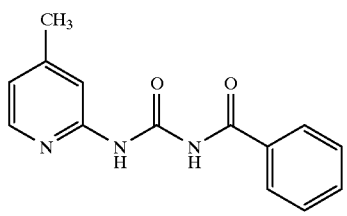

N-(2-(4-Methylpyridyl))-N'-benzoyl-urea

Benzoyl isocyanate (147 mg, 1 mmol) was added dropwise to a suspension of 2-amino-4-methylpyridine (108 mg, 1 mmol) in ether (10 mL) at room temperature. A precipitate formed instantaneously. After stirring 4 hours at room temperature, solid was filtered and washed with ether twice. The resulting white solid was dried in vacuo to give title compound (105 mg).

$^1$H NMR (D$_6$-DMSO)): 8.18 (d; J=5 Hz; 1H); 7.5–8.2 (br m, 5H); 7.13 (s; 1H); 6.98 (d; J=5 Hz; 1H); 2.34 (s; 3H).

EXAMPLE 15

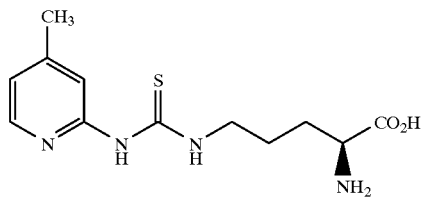

N-(2-(4-Methylpyridyl))-N'-(((S)-4-amino-4-carboxy)-n-butyl)-thiourea

Step A: N-(2-(4-Methylpyridyl))-N'-(((S)-4-t-butoxycarbonylamino-4-t-butoxycarbonyl)-n-butyl)-thiourea.

To a stirred mixture of 0.105 g (0.36 mmol) of N$^\alpha$(t-butoxycarbonyl)-(S)-ornithine t-butyl ester (Tet. Lett. 1991, 32, 875–878) in chloroform (2 mL) and CaCO$_3$ (0.11 g, 1.1 mmol) in water (2.5 mL) was added thiophosgene (42 uL, 0.55 mmol) at 0° C. The reaction was allowed to warm to room temperature and stirred for 45 min. The solution was diluted with methylene chloride and the layers were separated. The organic layer was washed with saturated salt solution, dried and concentrated to about 2 mL. This solution was transferred to a vial and 2-amino-4-methylpyridine (44 mg, 0.41 mmol ), triethylamine (70 uL, 0.5 mmol) and 4-dimethylaminopyridine (trace) were added. The vial was tighly capped and heated in a 40° C. bath over a weekend. The solution was cooled to room temperature and partitioned between water and methylene chloride. The methylene chloride layer was washed with saturated sodium bicarbonate, saturated salt solution, dried and concentrated by rotoevaporation. The residue was purified by preparative thin layer chromatography eluted with ethyl acetate to yield desired product (94 mg, 64% yield).

$^1$H NMR (CDCl$_3$) δ: 1.42 (s, 9H), 1.44 (s, 9H), 1.5–2.0 (m, 4H), 2.30 (s, 3H), 3.72 (m, 2H), 4.21 (m, 1H), 5.08 (d, 1H, J=8 Hz), 6.45 (s, 1H), 6.76 (d, 1H, J=4 Hz), 8.05 (d, 1H, J=4 Hz), 8.1 (br s, 1H).

Step B: N-(2-(4-Methylpyridyl))-N'-(((S)-4-amino-4-carboxy)-n-butyl)-thiourea.

Hydrogen chloride gas was passed through ethyl acetate (2 mL) at 0° C. until it was saturated. This solution (2 mL) was added to N-(2-(4-Methylpyridyl))-N'-(((S)-4-t-butoxycarbonylamino-4-t-butoxycarbonyl)butyl)-thiourea (from step A, 94 mg, 0.21 mmol) and the mixture was stirred for 20 h. A white solid was formed. The mixture was diluted with ether, the solid was filtered, washed with fresh ether and dried to yield the title compound as a hygroscopic solid (72 mg, 95% yield).

$^1$H NMR (CD$_3$OD) δ: 1.75–2.1 (m, 4H), 2.56 (s, 3H), 3.69 (t, 2H, J=6 Hz), 4.04 (t, 1H, J=6 Hz), 7.30 (s, 1H), 7.35 (d, 1H, J=6 Hz), 8.22 (d, 1H, J=6 Hz).

Mass Spectrum m/e=283 (M+1).

EXAMPLE 16

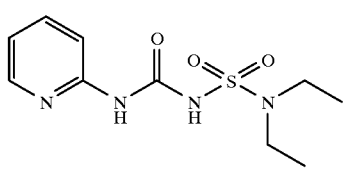

N-(2-Pyridyl)-N'-(diethylaminosulfonyl)-urea

This example was prepared according to the general procedure described by Karady et al. in *Heterocycles*, 1979, 12, 815–818. To a solution of 2-aminopyridine (5.0 g, 0.053 mol) in acetonitrile (17.5 mL) cooled to 0° C. was added chlorosulfonylisocyanate (4.5 mL) while maintaining the temperature between –5 and +5° C. A very thick precipitate formed. The cooling bath was removed, and the reaction mixture was allowed to warm to room temperature. The mixture was re-cooled to 0° C., and diisopropylethylamine (8 mL, 0.046 mol) was added dropwise with stirring while maintaining the internal temperature between –5 and +5° C. An additional 0.85 mL of diisopropylethylamine was added, and the mixture was allowed to warm to room temperature and stirred overnight. The solid that formed was filtered, washed with cold acetonitrile, and dried in vacuo; yield 6.0 g. To a mixture of this 1,2,4,6-thiatriazene-1,1-dioxide (2.0 g, 0.010 mol) in acetonitrile (60 mL) was added diethylamine (0.97 mL, 9.38 mmol). The reaction mixture was stirred overnight at room temperature and evaporated. The resulting solid was triturated with methanol, filtered, washed with diethyl ether, and dried in vacuo; yield 1.6 g (55%).

$^1$H NMR (CD$_3$OD) δ: 1.20 (t, 3H), 3.42 (q, 2H), 7.06 (dd, 1H), 7.22 (br m, 1H), 7.76 (m, 1H), 8.23 (m, 1H).

Mass Spectrum m/e=273 (M+1).

EXAMPLE 17

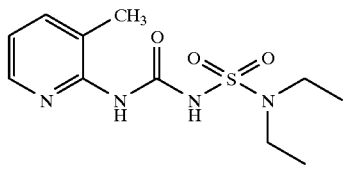

N-(2-(3-Methylpyridyl)-N'-(diethylaminosulfonyl)-urea

This example was prepared in a manner analogous to that described for the preparation of Example 16, but substituting 2-amino-3-picoline in place of 2-aminopyridine.

$^1$H NMR (CD$_3$OD) δ: 1.20 (t, 3H), 2.29 (s, 3H), 3.43 (q, 2H), 7.04 (dd, 1H), 7.65 (d, 1H), 8.12 (d, 1H).

Mass Spectrum m/e=287 (M+1).

EXAMPLE 18

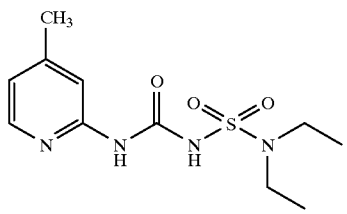

N-(2-(4-Methylpyridyl)-N'-(diethylaminosulfonyl)-urea

This example was prepared in a manner analogous to that described for the preparation of Example 16, but substituting 2-amino-4-picoline in place of 2-aminopyridine.

$^1$H NMR (CD$_3$OD) δ: 1.20 (t, 3H), 2.33 (s, 3H), 3.42 (q, 2H), 6.91 (d, 1H), 7.02 (br s, 1H), 8.09 (d, 1H).

Mass Spectrum m/e=287 (M+1).

EXAMPLE 19

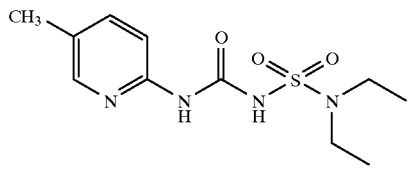

N-(2-(5-Methylpyridyl)-N'-(diethylaminosulfonyl)-urea

This example was prepared in a manner analogous to that described for the preparation of Example 16, but substituting 2-amino-5-picoline in place of 2-aminopyridine.

$^1$H NMR (CD$_3$OD) δ: 1.20 (t, 3H), 2.29 (s, 3H), 3.42 (q, 2H), 7.12 (br s, 1H), 7.60 (dd, 1H), 8.08 (d, 1H).

Mass Spectrum m/e=287 (M+1).

EXAMPLE 20

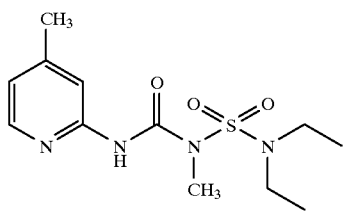

N-(2-(4-Methylpyridyl)-N'-(diethylaminosulfonyl)-N'-methyl-urea

To a solution of N-(2-(4-methylpyridyl)-N'-(diethylaminosulfonyl)-urea (100 mg, 0.349 mmol) in 4:1 benzene-methanol (2 mL) was added (trimethylsilyl) diazomethane (2.0 M solution in hexanes, 0.175 mL, 0.35 mmol). The reaction mixture was stirred for one hour at room temperature and then evaporated. Pure title compound was obtained after chromatography on silica gel (25% acetone/hexane as eluant); yield 85 mg (81%).

$^1$H NMR (CDl$_3$OD) δ: 1.20 (t, 3H), 2.38 (s, 3H), 3.20 (s, 3H), 3.40 (q, 2H), 6.97 (d, 1H), 7.88 (s, 1H), 8.09 (d, 1H).

Mass Spectrum m/e=301 (M+1).

EXAMPLE 21

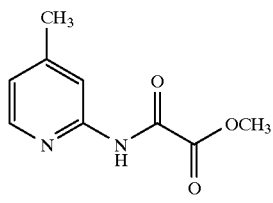

Oxalamide, N-(4-methyl-2-pyridyl), methyl ester

To a solution of 2-amino-4-picoline (500 mg, 4.62 mmol) in methylene chloride (15 mL) cooled in an ice-bath were added triethylamine (1.4 mL, 0.010 mol) followed by a solution of methyl oxalyl chloride (0.467 mL, 5.08 mmol) in methylene chloride (5 mL) dropwise with stirring. The reaction mixture was stirred for one hour at ice temperature, diluted with methylene chloride, washed with water, saturated sodium bicarbonate solution, saturated brine solution, dried (Na$_2$SO$_4$), and evaporated. Pure title compound was obtained as a white solid after chromatography on silica gel (5% acetone/hexane as eluant); yield 195 mg (22%).

$^1$H NMR (CD$_3$OD) δ: 2.37 (s, 3H), 3.74 (s, 3H), 6.98 (d, 1H), 7.95 (br s, 1H), 8.12 (d, 1H).

Mass Spectrum m/e=195 (M+1).

EXAMPLE 22

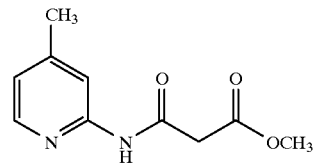

Malonamide, N-(4-methyl-2-pyridyl), methyl ester

To a solution of 2-amino-4-picoline (500 mg, 4.62 mmol) in tetrahydrofuran (15 mL) cooled in an ice-bath were added triethylamine (0.710 mL, 5.09 mmol) followed methyl malonyl chloride (0.520 mL, 4.85 mmol) dropwise with stirring. The cooling bath was removed, and the reaction mixture was stirred overnight at room temperature. The mixture was partitioned between ethyl acetate and water. The organic layer was washed with 2N hydrochloric acid, saturated sodium bicarbonate solution, saturated brine solution, dried (Na$_2$SO$_4$), and evaporated. Pure title compound was obtained as a white solid after chromatography on silica gel (30% ethyl acetate/hexane as eluant); yield 535 mg (56%).

$^1$H NMR (CD$_3$OD) δ: 2.39 (s, 3H), 3.32 (s, 2H), 3.93 (s, 3H), 7.07 (d, 1H), 7.99 (br s, 1H), 8.19 (d, 1H).

Mass Spectrum m/e=209 (M+1).

Isolation and Purification of Nitric Oxide Synthases

Methods demonstrating the isolation and purification of all three isoforms of NOS have been published and reviewed in U. Forstermann, J. S. Pollock, W. R. Tracey, M. Nakane in *Methods in Enzymology*, Vol. 233, L. Packer, ed., Academic Press, NY, 1994, Ch.26, pp. 258–264. Cloned and expressed NOS has also been demonstrated and reviewed in C. J Lowenstein and S. H. Snyder in *Methods in Enzymology*, Vol. 233, L. Packer, ed., Academic Press, NY, 1994, Ch.26, pp. 264–269.

Assay Protocol for NOS activity

Various assays for NOS activity have been reported in the literature and are reviewed in the following: M. E. Murphy and E. Noack in *Methods in Enzymology*, Vol. 233, L. Packer, ed., Academic Press, NY, 1994, Ch.26, pp. 240–250 and J. M. Hevel and M. A. Marletta in *Methods in Enzymology*, Vol. 233, L. Packer, ed., Academic Press, NY, 1994, Ch.26, pp. 250–258. Details for the assay protocols to measure NOS activity are as follows:

NOS activity is measured as the formation of L-[2,3,4,5-$^3$H]Citrulline from L-[2,3,4,5-$^3$H]Arginine. The incubation buffer (100 μL) contained; 100 mM TES, pH 7.5, 5 μM FAD, 5 μM FMN, 10 μM $BH_4$, 0.5 mM NADPH, 0.5 mM DTT, 0.5 mg/mL BSA, 2 mM CaCl2, 10 μg/mL calmodulin (bovine), 1 μM L-Arg, 0.2 μCi L-[2,3,4,5-$^3$H]Arg, and the inhibitor in aqueous DMSO (max. 5 %). The reaction is initiated by addition of enzyme. Incubations are performed at room temperature for 30 minutes and stopped by the addition of an equal volume of quenching buffer consisting of 200 mM sodium citrate, pH 2.2, 0.02% sodium azide. Reaction products are separated by passing through a cation exchange resin and quantitated as cpm by scintillation counting. Percent inhibition is calculated relative to enzyme incubated without inhibitor according to: % inhibition =100×(cpm L-[2,3,4,5-$^3$H]Cit with inhibitor/cpm L-[2,3,4,5-$^3$H]Cit without inhibitor).

Illustrative of the utility of the compounds of Formula I is the ability of such compounds to inhibit NO synthase as shown in Table 1 and as measured by the assay described above:

TABLE 1

Inhibition of Human Inducible Nitric Oxide Synthase by 2-Acylamino-Pyridines

| Example No | % inh. @ 50 μM | $IC_{50}$ (μM) |
|---|---|---|
| 1 | 54 | <50 |
| 2 | 63 | <50 |
| 3 | 75 | <50 |
| 4 | 86 | <10 |
| 5 | 51 | <50 |
| 6 | 100 | <1 |
| 7 | 100 | <10 |
| 8 | 50 | ND* |
| 9 | 55 | <50 |
| 10 | 54 | ND |
| 11 | 70 | <50 |
| 12 | 76 | <50 |
| 13 | 57 | <50 |
| 14 | 96 | <10 |
| 15 | 85 | <10 |
| 16 | 55 | <10 |
| 17 | 100 | <10 |
| 18 | 92 | <1 |
| 19 | 100 | <50 |
| 20 | 100 | <1 |
| 21 | 100 | <1 |
| 22 | 57 | >50 |

*ND = Not determined.

What is claimed is:

1. A compound of Formula (I)

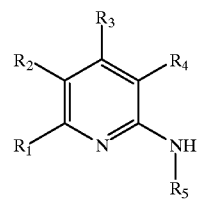

(I)

or a pharmaceutically acceptable salt thereof wherein:

one of $R_1$ and $R_2$, $R_2$ and $R_3$ or $R_3$ and $R_4$ including the optional substituents present thereon, is joined together to form a 5-, 6- or 7-membered saturated monocyclic ring containing 0, 1 or 2 heteroatoms which together with the atoms to which $R_1$ and $R_2$, or $R_2$ and $R_3$ or R3 and $R_4$ are attached there is formed a bicyclic ring according to Formulae (IIa–IIc), the heteroatoms being selected from the group consisting of O, S and N,

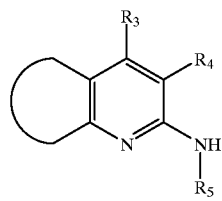

(IIa)

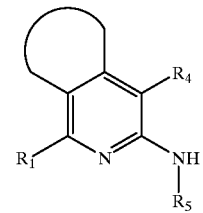

(IIb)

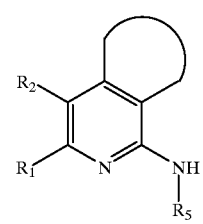

(IIc)

and wherein the rings of Formulae IIa, IIb and IIc are selected from the group consisting of

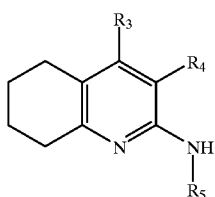 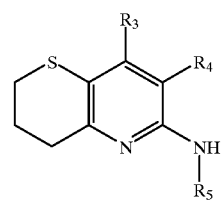

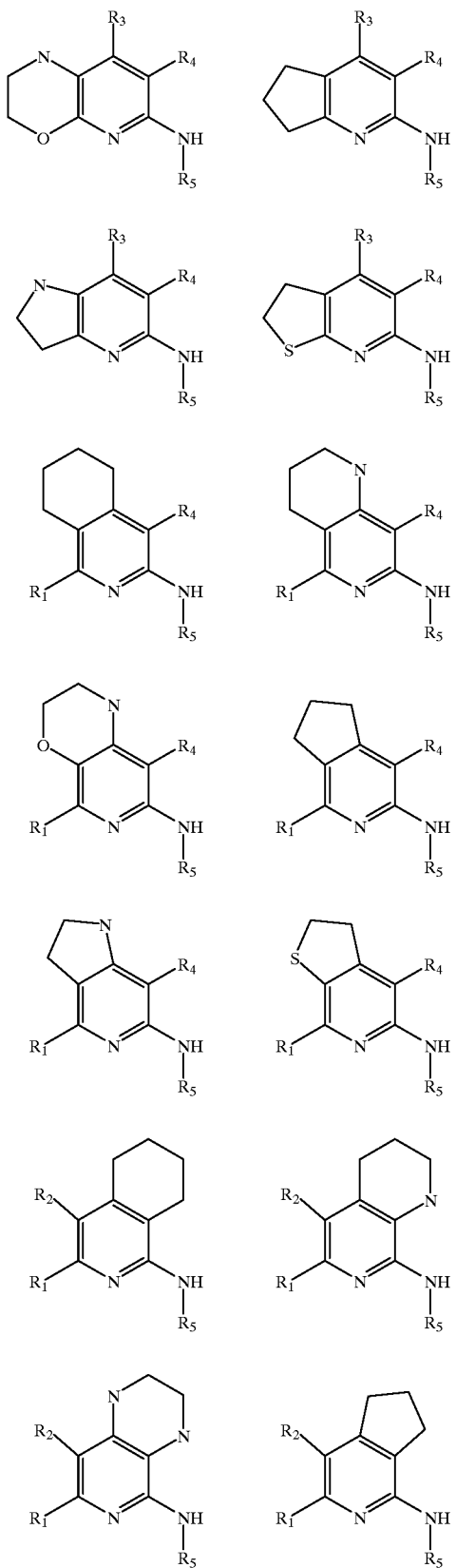

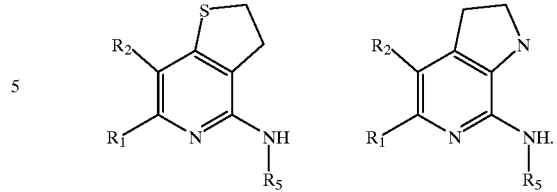

and the remaining $R_1$, $R_2$, $R_3$ and $R_4$ groups are each independently selected from the group consisting of:
(a) hydrogen,
(b) hydroxy,
(c) amino,
(d) cyano,
(e) halo selected from the group consisting of: fluoro, chloro, bromo, and iodo,
(f) trifluoromethyl,
(g) $C_{1-6}$alkyl,
(h) $C_{1-6}$alkoxy,
(i) $C_{1-6}$alkylthio,
(j) $C_{1-6}$alkylcarbonyl,
(k) mono- and di-$C_{1-6}$alkylamino,
(l) aryl, where aryl is phenyl and naphthyl,
(m) aryloxy, where aryl is phenyl and naphthyl,
(n) cycloalkyl, wherein the cycloalkyl is a 5-, 6-, or 7-membered monocyclic ring which optionally contains 1 or 2 heteroatoms selected from S, O, and N,
(o) heteroaryl, wherein heteroaryl is selected from the group consisting of:
  (1) pyridyl,
  (2) furanyl,
  (3) thienyl,
  (4) pyrazinyl,
  (5) pyrimidyl,
  (6) thiazolyl, and
  (7) triazolyl,
each of (g) to (o) being optionally mono- or disubstituted, the substituents being independently selected from:
  (1) hydroxy,
  (2) $C_{1-4}$alkyl,
  (3) C1-3alkoxy,
  (4) amino,
  (5) mono- and di-$C_{1-6}$alkylamino,
  (6) carboxyl,
  (7) $C_{1-3}$alkylthio,
  (8) $C_{1-3}$alkyl-S(O)$_k$—, where k is 1 or 2,
  (9) $C_{1-4}$alkoxycarbonyl,
  (10) halo selected from the group consisting of: fluoro, chloro, bromo, and iodo,
  (11) oxo and
  (12) amidino, and
$R_5$ is selected from the group consisting of
(a) amino-C(=S)—,
(b) $C_{1-6}$alkylcarbonyl,
(c) aroyl, wherein the aroyl group is benzoyl,
(d) $C_{1-6}$alkylamino-C(=S)—,
(e) $C_{2-6}$alkenylamino-C(=S)—,
(f) arylamino-C(=S)—, wherein the aryl group is phenyl and naphthyl (g) arylC1–6alkylamino-C(=S)—, wherein the aryl group is phenyl and naphthyl,
(h) cycloC$_{5-7}$alkylamino-C(=S)—,
(i) aroylaminocarbonyl, wherein the aroyl group is benzoyl and naphthoyl,
(j) R$_6$R$_7$N—SO$_2$—NH—C(=O)—, wherein R$_6$ and R$_7$ are independently selected from the group consisting of
  (1) hydrogen,
  (2) C$_{1-6}$alkyl
  (3) aryl, wherein the aryl group is selected from phenyl,
  (4) R$_6$ and R$_7$ may be joined together to form a 5-, 6- or 7-membered ring containing 0, 1 or 2 heteroatoms, the heteroatoms being elected from the group of oxygen, sulfur and nitrogen,
each of (b) to (j) being optionally mono- or di- substituted, the substituents being independently selected from
  (1) hydroxy,
  (2) C$_{1-4}$alkyl,
  (3) C$_{1-3}$alkoxy,
  (4) amino,
  (5) mono- and di-C$_{1-6}$alkylamino,
  (6) carboxyl,
  (7) C$_{1-3}$alkylthio,
  (8) C$_{1-3}$alkyl-S(O)$_k$—, where k is 1 or 2,
  (9) C$_{1-4}$alkoxycarbonyl,
  (10) halo selected from the group consisting of: fluoro, chloro, bromo, and iodo,
  (11) oxo, and
  (12) amidino.

2. A compound according to claim 1 wherein the remaining R$_1$, R$_2$, R$_3$ and R$_4$ groups are each independently selected from the group consisting of:
  (a) hydrogen,
  (b) hydroxy,
  (c) amino,
  (d) cyano,
  (e) fluoro, chloro or bromo,
  (f) trifluoromethyl,
  (g) C$_{1-4}$alkyl,
  (h) C$_{1-4}$alkoxy,
  (i) C$_{1-4}$alkylthio,
  (j) mono- and di-C$_{1-4}$alkylamino, and
R$_5$ is selected from the group consisting of
  (a) amino-C(=S)—,
  (b) C$_{1-4}$alkylamino-C(=S)—,
  (c) C$_{2-4}$alkenylamino-C(=S)—,
  (d) arylamino-C(=S)—, wherein the aryl group is phenyl and naphthyl,
  (e) arylC1–4alkylamino-C(=S)—, wherein the aryl group is phenyl,
  (f) R$_6$R$_7$N—SO$_2$—NH—C(=O)—, wherein R$_6$ and R$_7$ are independently selected from the group consisting of
    (1) hydrogen,
    (2) C$_{1-4}$alkyl
    (3) phenyl,
each of (b) to (f) being optionally mono- or di- substituted, the substituents being independently selected from
  (1) hydroxy,
  (2) C1 4alkyl,
  (3) C$_{1-3}$alkoxy,
  (4) amino,
  (5) mono- and di-C$_{1-6}$alkylamino,
  (6) carboxyl,
  (7) C$_{1-3}$alkylthio, and
  (8) halo selected from the group consisting of: fluoro, chloro and bromo.

3. A compound according to claim 2 wherein
R$_2$ is hydrogen or methyl,
R$_4$ is hydrogen or methyl,
R$_1$ and R$_3$ are each independently selected from
  (a) hydrogen,
  (b) methyl, ethyl, propyl or butyl,
  (c) chloro,
  (d) —CN, and
  (e) —CF$_3$,
R$_5$ is selected from the group consisting of
  (a) amino-C(=S)—,
  (b) C$_{1-4}$alkylamino-C(=S)—,
  (c) C$_{2-4}$alkenylamino-C(=S)—,
  (d) arylamino-C(=S)—, wherein the aryl group is phenyl and naphthyl,
  (e) arylC1–4alkylamino-C(=S)—, wherein the aryl group is phenyl,
  (f) R$_6$R$_7$N—SO$_2$—NH—C(=O)—, wherein R$_6$ and R$_7$ are independently selected from the group consisting of
    (1) hydrogen,
    (2) C$_{1-2}$alkyl,
    (3) phenyl,
  each of (b) to (f) being optionally mono- or di-substituted, the substituents being independently selected from
    (1) hydroxy,
    (2) C$_{1-2}$alkyl,
    (3) C$_{1-2}$alkoxy,
    (4) amino,
    (5) mono- and di-C$_{1-3}$alkylamino,
    (6) C$_{1-3}$alkylthio,
    (7) halo selected from fluoro, chloro and bromo.

4. A pharmaceutical composition for treating a nitric oxice synthase mediated disease comprising a pharmaceutical carrier and a non-toxic effective amount of the compound of claim 1.

5. A method for inhibiting the activity of nitric oxide synthases comprising administering to a subject suffering from a nitric oxide synthase mediated disease, a non-toxic therapeutically effective amount of the compound of claim 1.

6. A pharmaceutical composition for treating a nitric oxide synthase mediated disease comprising a pharmaceutical carrier and a non-toxic effective amount of the compound selected from
  (a) N-(2-(4-Methylpyridyl))-N'-(4-methylphenyl)-urea;
  (b) N-(2-(4-Methylpyridyl))-thiourea;
  (c) N-(2-(4,6-dimethylpyridyl))-thiourea;
  (d) N-(2-(5-trifluoromethylpyridyl))-N'-allyl-thiourea;
  (e) N-(2-(4,6-dimethylpyridyl))-N'-allyl-thiourea;
  (f) N-(2-(4-Methylpyridyl))-N'-isopropyl-thiourea;
  (g) N-(2-(4-Methylpyridyl))-N'-ethyl-thiourea;
  (h) N-(2-(4-Methylpyridyl))-N'-phenyl-thiourea;
  (i) N-(2-Pyridyl)-N'-(4-bromophenyl)-thiourea;
  (j) N-(2-(4-Methylpyridyl))-N'-(1-naphthyl)-thiourea;
  (k) N-(2-(4-Methylpyridyl))-N'-(3-fluorophenyl)-thiourea;
  (l) N-(2-(4-Methylpyridyl)-N'-benzyl-thiourea;
  (m) N-(2-(4-Methylpyridyl))-N'-(3,3,5-trimethylcyclohexyl)-thiourea;

(n) N-(2-(4-Methylpyridyl))-N'-benzoyl-urea; and
(o) N-(2-(4-Methylpyridyl))-N'-(((S)-4-amino-4-carboxy)-n-butyl)-thiourea;
(p) N-(2-Pyridyl)-N'-(1-piperazinylsulfonyl)-urea;
(q) N-(2-(3-Methylpyridyl)-N'-(diethylaminosulfonyl)-urea;
(r) N-(2-(4-Methylpyridyl)-N'-(diethylaminosulfonyl)-urea;
(s) N-(2-(5-Methylpyridyl)-N'-(diethylarninosulfonyl)-urea;
(t) N-(2-(4-Methylpyridyl)-N'-(diethylaminosulfonyl)-N'-methyl-urea;
(u) Oxalamide, N-(4-methyl-2-pyridyl), methyl ester; and
(v) Malonamide, N-(4-methyl-2-pyridyl), methyl ester.

* * * * *